United States Patent [19]

Hagen

[11] Patent Number: 5,354,273
[45] Date of Patent: Oct. 11, 1994

[54] DELIVERY APPARATUS WITH PRESSURE CONTROLLED DELIVERY

[75] Inventor: Ronald W. Hagen, St. Charles, Mo.

[73] Assignee: Mallinckrodt Medical, Inc., St. Louis, Mo.

[21] Appl. No.: 988,266

[22] Filed: Dec. 14, 1992

[51] Int. Cl.5 ............................................. A61M 31/00
[52] U.S. Cl. ........................................ 604/66; 604/67; 128/DIG. 12
[58] Field of Search ................................... 604/65–67; 128/DIG. 1, DIG. 12

[56] References Cited

U.S. PATENT DOCUMENTS

| | | |
|---|---|---|
| 2,702,547 | 2/1955 | Glass . |
| 3,623,474 | 11/1971 | Hoffman . |
| 3,701,345 | 10/1972 | Hellman et al. . |
| 3,720,211 | 3/1973 | Kyrias . |
| 3,812,843 | 5/1974 | Wootten et al. . |
| 3,880,138 | 4/1975 | Wootten et al. . |
| 3,888,239 | 6/1975 | Rubinstein . |
| 3,993,061 | 11/1976 | O'Leary . |
| 3,993,065 | 11/1976 | Szabo et al. . |
| 4,006,736 | 2/1977 | Kranys et al. . |
| 4,323,066 | 4/1982 | Bourdon . |
| 5,112,317 | 5/1992 | Michel . |
| 5,242,408 | 9/1993 | Shuboo et al. ..................... 604/67 |
| 5,244,461 | 9/1993 | Derlien ..................... 128/DIG. 12 |

Primary Examiner—Jerome L. Kruter
Attorney, Agent, or Firm—Rothwell, Figg, Ernst & Kurz

[57] ABSTRACT

A delivery apparatus for delivering various media, such as medical and/or pharmaceutical media or the like, from a delivery device, such as a syringe, in which the delivery pressure of the medium as it is dispensed from the delivery device is automatically maintained and regulated at a preselected level throughout delivery of the medium from the delivery apparatus. In one embodiment, the skin temperature of the patient is also sensed and the pressure of the medium being administered to the patient is further adjusted in response to the sensed skin temperature.

10 Claims, 2 Drawing Sheets

DELIVERY APPARATUS WITH PRESSURE CONTROLLED DELIVERY

FIELD OF THE INVENTION

The present invention relates to delivery apparatus for use with and incorporating delivery devices such as syringes and the like for delivery of various media such as fluids in the form of liquids and/or gases, fluids containing solid particulates, pharmaceutical media such as suspensions of gas filled microspheres and the like. More particularly, the present invention relates to prefilled delivery apparatus utilizing and including delivery devices of the aforementioned type in which the medium being dispensed from the device is sensitive to the pressure at which the medium is dispensed.

DESCRIPTION OF THE PRIOR ART

In delivery devices such as syringes and the like, the medium being dispensed is in some cases sensitive to the pressure at which the medium is dispensed from the device. For example, in the case of certain pharmaceutical media such as suspensions of gas filled microspheres and the like, the medium itself may be sensitive to pressure. In other cases, the rate at which the medium is dispensed from the device may be particularly sensitive to the pressure at which the medium is expelled from the device or the force at which the dispensing piston is driven.

In prior art devices, the control of such pressures and forces was effected by manual means and by relying on the sense of feel in order to attain and realize the proper dispensing conditions based on subjective judgment factors. The proper dispensing of the medium was therefore dependent upon the experience of the person handling the device and the skill and judgment applied in the operation thereof, and was often subject to wide variations in results with differing degrees of effectiveness as well as to the possibility of human error.

SUMMARY OF THE INVENTION

The present invention provides a delivery apparatus which includes means for receiving and holding a delivery device, such as a syringe containing a medium which is to be dispensed from the syringe, and which provides a mechanism for applying a controlled force to the delivery mechanism of the syringe to generate and maintain a controlled pressure of delivery of the medium from the syringe. The apparatus includes means for sensing the force applied to the delivery mechanism of the syringe and feedback control means for regulating the applied force to maintain a selected level, which is set as a reference level for the system. Once the system is set to the desired force and resultant pressure level for the delivery of the medium from the syringe, the system automatically applies the selected control force to the syringe and maintains the preset control force throughout the delivery stroke of the syringe. The system thus operates automatically, without any need for or reliance on human judgment factors or operator skills, to attain a highly precise pressure control throughout the delivery stroke of the syringe.

In one embodiment of the invention, the delivery pressure of the medium is sensed as it is delivered from the delivery apparatus and/or at the point of actual injection into a patient and a signal proportional to the delivery pressure is also fed back to provide an additional control over the control force which is applied to the medium in the delivery device.

In a further embodiment, the temperature of the patient, preferably the temperature of the skin of the patient to whom the medium is being administered, is sensed and also used as a further parameter for adjusting the pressure level at which the medium is dispensed.

DETAILED DESCRIPTION OF THE PREFERRED EMBODIMENTS

Figure 1:
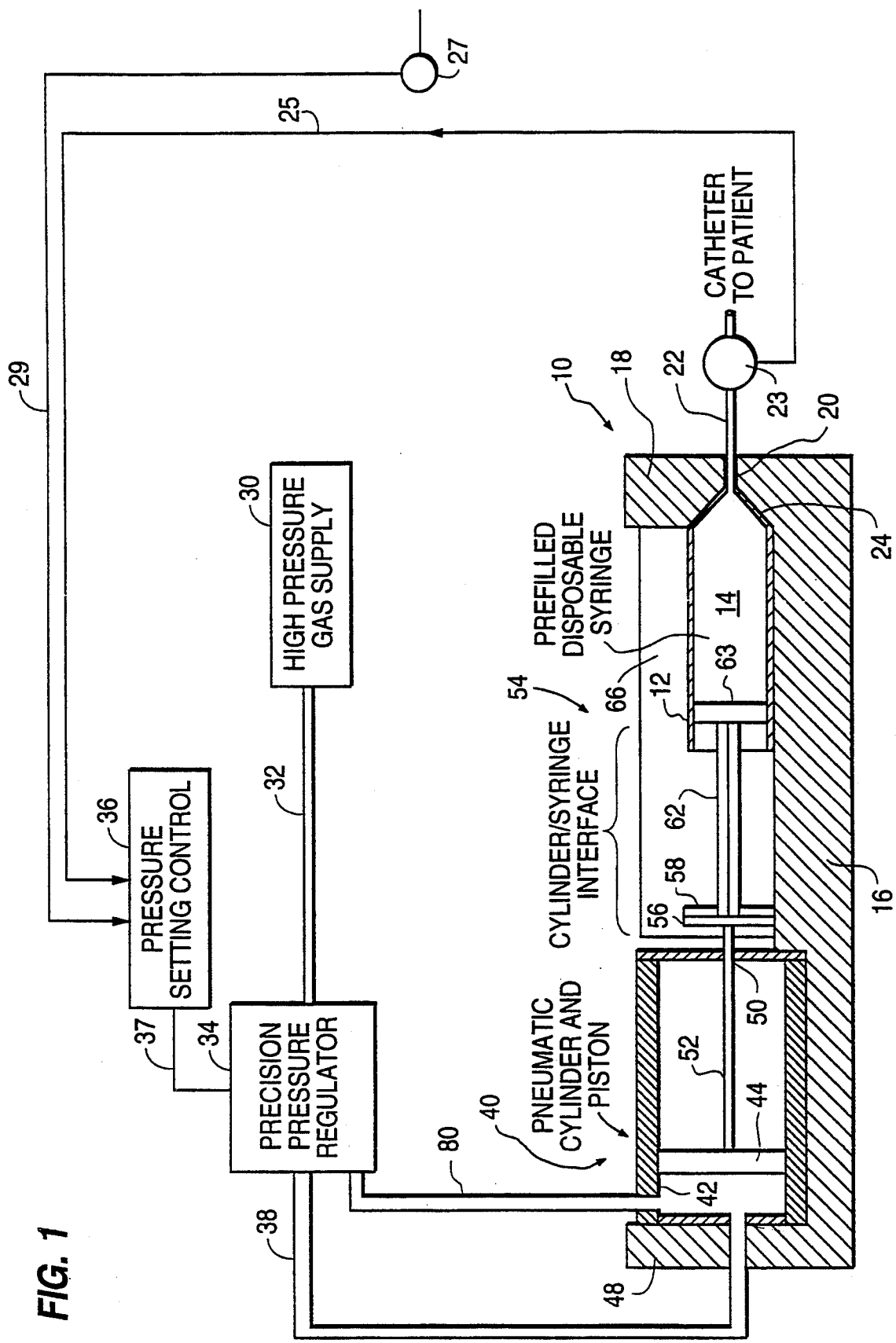
FIG. 1 is a side view, taken partly in cross section, of a pressure controlled delivery apparatus embodying the present invention.

Referring to the embodiment of FIG. 1, there is shown a pressure controlled delivery apparatus 10 having mounted therein a delivery device apparatus 12 which is of the prefilled type such as but not limited to the type disclosed, for example, in U.S. Pat. Nos. 4,628,969— Jurgens, Jr. et. al., and 4,718,463—Jurgens, Jr. et. al. Contained within a container of the delivery device apparatus 12 is a pharmaceutical medium 14 in the form of a fluid, for example, or a suspension in a fluid of gas filled microspheres or the like, which may be sensitive to pressure.

The delivery device apparatus 12 is mounted for use in the pressure controlled delivery apparatus 10 to enable the medium 14 to be ejected from the container of the delivery device apparatus at a controlled pressure and/or at a controlled rate dependent upon the delivery pressure. The apparatus 10 is formed of an open frame element 16 which includes at one end thereof an upright portion 18 having an aperture 20 through which a delivery tip 22 of the delivery device apparatus 12 protrudes. The aperture 20 is formed with a conically shaped portion 24 which engages the conically shaped delivery end of the syringe 12 as it tapers down to the diameter of the delivery tip 22.

In the embodiment of FIG. 1, actuating power for the apparatus is supplied by a high pressure gas supply 30, which is connected by line 32 to supply actuating gas under controlled pressure through a precision pressure regulator 34. The reference pressure level at which the regulator 34 is set to control pressure of the actuating gas is set by means of a pressure setting control 36 which supplies a reference signal at line 37. The pressure setting control 36 may be set manually or by any other means to a selected reference pressure at which the regulator 34 provides actuating gas at an outlet to a gas connection line 38 thereof. The gas at the regulated pressure gas connection line 38 is connected to a pneumatic compartment and piston apparatus 40, which is comprised of a compartment 42 and a piston 44 slidably mounted therein. The compartment and piston apparatus 40 is mounted in the frame member 16 and secured to an end wall 48 thereof at the opposite end of the frame member 16 from the end wall 18. Extending from the piston 44 and through an opening 50 in the opposite end of the compartment 42 is a piston actuating rod 52. The piston rod 52 extends into a compartment/delivery device interface region 54 where it is provided with a foot member 56 formed to engage an end member 58 of a delivery mechanism, such as a push rod or like member 62, of the delivery device apparatus 12. In one embodiment, a push rod 62 is connected to a piston 63 which is slidably mounted in the in the delivery device apparatus 12 for purposes of dispensing the fluid 14 from the delivery device apparatus. The prefilled, disposable delivery device apparatus 12, in the embodiment shown in FIG. 1, is mounted for use in a preferably arcuate cradle 66 formed in the frame member 16. In an alternative embodiment, foot member 56 is formed to engage end member 58 of the delivery device apparatus 12, which is formed of a flexible collapsible material and which is caused to collapse for purposes of delivering the fluid 14 contained therein.

As mounted for use as shown, the delivery device apparatus 12 engages the conically shaped outlet portion 24 formed in the end wall 18 of the frame member 16. The delivery tip portion 22 of the syringe 12 extends through the opening 20 in the end wall 18 and is connected to deliver the stored fluid 14 from the barrel of the syringe through the delivery tip portion 22 for the selected end use thereof, such as, for example, to a catheter connected to a patient.

The level of the pressure on the piston 44 in the compartment 42 as delivered from the regulator 34 through the line 38 is fed back to the regulator 34 by means of a feedback connecting line 80. The actual pressure level in the compartment 42 is fed back to the regulator 34 and compared with the selected pressure level as set by the pressure setting control 36 and regulated by feedback control exactly to the level set by the setting control 36.

In the embodiment of FIG. 1, the magnitude of the pressure in the compartment 42, and hence the magnitude of the force exerted on the piston 44, is sensed by force sensing means in the form of means for sensing the pressure level in the line 38, which pressure sensing means is a part of the regulator 34. The regulator 34 also includes comparator means for comparing the reference pressure or force signal from the pressure setting control 36 at line 37 with the sensed pressure or force on the piston 44 as sensed by the force sensing means responsive to the magnitude of the pressure in line 38. Thus, the magnitude of the actual force on the piston 44, in the form of the magnitude of the pressure in compartment 42 as sensed at line 38, is compared with the set reference level signal at line 37 in the comparator means in the pressure regulator 34, and the regulator 34 responds to the difference between the actual sensed force level and the reference force level to reduce the difference or error signal to zero, thereby maintaining the regulated pressure at line 38 at the set reference level.

In the embodiment of FIG. 1, a pressure and/or temperature sensing element 23 (shown connected as a pressure sensing element) may also be provided at the output end 22 of the delivery device apparatus 12 to sense the actual pressure level of the fluid as it is dispensed from the apparatus and to provide an output pressure signal at an output line 25 thereof. The output pressure level signal, as sensed by the pressure sensing element 23, is fed back through the output signal line 25 to the pressure setting control to effect an adjustment of the reference pressure setting level depending upon the desired pressure level at the delivery tip portion 22 as sensed by the pressure sensing element 23. This desired level is also set in the pressure setting control 36.

A still further pressure and/or temperature monitor may be provided to sense the pressure level of the medium being dispensed at the point where it is actually delivered for use, that is, for example at the point of injection into a patient, and to sense the skin temperature of the patient. The pressure at this point, which may include the pressure at or in the veins of the patient, is sensed by a pressure and/or temperature sensing element 27 and an output signal is connected therefrom through a line 29 to the pressure setting control 36 to provide a further adjustment of the reference pressure level setting responsive to the pressure of the medium at the actual delivery point. The desired pressure level at the delivery point is also set in the pressure setting control 36 and the reference pressure level is further adjusted according to this parameter.

The pressure setting control can also be programmed to effect a complete shut-down of the delivery apparatus if the pressure sensed at either of the pressure sensing elements 23 or 27 exceeds a preselected level as set in the pressure setting control 36.

The operation of the embodiment of FIG. 1 is as follows.

The delivery device apparatus 12 containing the fluid 14 to be dispensed is first inserted in the apparatus in the arcuate cradle 66 with the conical end thereof in engagement with the conically shaped opening 24 in the end wall 18. In this position, the delivery device apparatus 12 rests on the bottom surface of the arcuate cradle 66 with the delivery tip portion 22 thereof extending through the opening 20 for connection to dispensing apparatus such as a catheter.

The delivery device apparatus 12 is mounted with the end member 58 of the push rod 62 thereof positioned to engage the foot member 56 of the piston rod 52. After the delivery device apparatus 12 has been so mounted as just described, the desired pressure at which the contents 14 of the delivery device apparatus are to be dispensed is set at the pressure setting control 36 and the system is activated at the pressure setting control. Upon activation as just described, the pressure regulator 34 controls the gas flow from the high pressure gas supply 30 through the regulator 34 and through the gas connection line 38 to the compartment 42. The pressure of the gas delivered to the compartment 42 through the line 38 is precisely regulated to the level set at the pressure setting control 36 so that the force applied by the piston 44 through the piston rod 52 is correspondingly regulated and held precisely at the preselected level which corresponds to the regulated pressure setting.

A precisely regulated force is thus applied through the piston rod 52 and through the flanges 56 and 58 to the push rod 62 and piston 63 of the syringe 12, whereby the contents 14 of the syringe 12 are delivered through the delivery tip portion 22 at the precisely regulated pressure as set at pressure setting control 36 throughout the entire stroke of the push rod 62.

As explained above, the reference pressure level set in the pressure setting control 36 is also further automatically adjusted by the signals at lines 25 and 28 from the pressure sensing elements 23 and 27.

Figure 2:
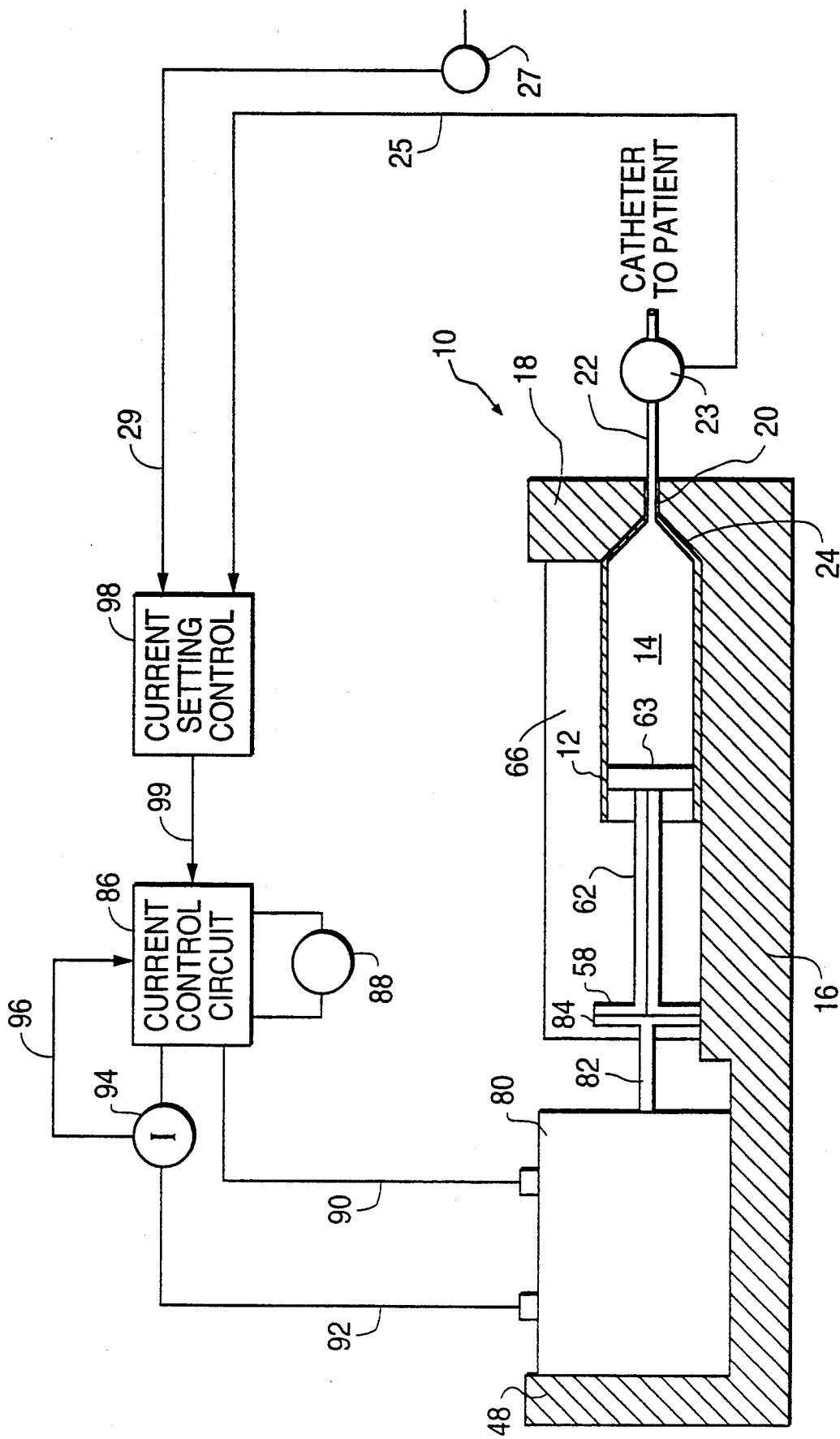
FIG. 2 is a side view, taken partly in cross section, of a pressure controlled delivery apparatus incorporating another embodiment of the present invention.

Another embodiment of the present invention is shown in FIG. 2, in which an alternative form of force application means is employed to generate the controlled force for expelling the contents from the syringe 12. In this embodiment, an electric torque motor means 80 is mounted in the frame member 16 in a position which replaces the pneumatic piston and compartment apparatus 40 of the embodiment of FIG. 1.

The electric torque motor means 80 is of a well known type and delivers an output torque which is proportional to the input current to the motor. The torque motor means 80 includes an internal gear mechanism which converts the rotary motion of the motor to a linear output motion of an output rod 82. That is, the torque generated by the torque motor in the torque motor means 80 is converted to a linear force which is applied in the direction of the axis of the output rod 82. The output rod 82 of the motor 80 is provided with a flange portion 84 which engages the flange 58 of the push rod 62 of the delivery device apparatus 12 when the apparatus is mounted in place within the assembly.

The remaining elements of the assembly 10 of the embodiment of FIG. 2 are substantially the same as those in the embodiment of FIG. 1. That is, the torque motor assembly 80 is mounted in the frame member 16 and replaces the piston and compartment apparatus 40 of the embodiment of FIG. 1 to supply the actuating force to the syringe 12.

The torque motor means 80 is controlled by means of a motor current control circuit 86 which is connected to an electrical power supply 88. Electrical power is connected from the output of the motor current control circuit 86 to the motor means 80 by lines 90 and 92. The magnitude of the current flowing to the motor means 80 through the lines 90 and 92 is measured by a current sensing means 94 which feeds back to the motor current control 86 through line 96 a signal proportional to the current flowing to the motor means 80 as sensed by the current sensing means 94.

A selected magnitude for the current to be delivered to the motor means 80 is set at a current setting control 98, which establishes a reference current magnitude at line 99 which the current to the motor means 80 is to be regulated and maintained. The selected reference current magnitude is set at the current setting control 98 by an operator of the system and, since the current delivered to the motor means 80 is directly proportional to the force output at the shaft 82 thereof, the reference setting so selected by the operator represents a selected force magnitude which is to be applied at the output shaft 82 to the push rod 62 of the delivery device apparatus 12. Accordingly, the current setting control 98 is calibrated in terms of a selected force or pressure level at which the fluid 14 is to be delivered from the delivery device apparatus 12.

Again, as in the case of the embodiment of FIG. 1, the output pressure of the delivery apparatus may also be sensed by means of a pressure sensing element 23 and a signal proportional thereto fed back through line 25 to the current setting control 98 to further adjust the reference pressure level in accordance with a selected output pressure for the output pressure at the delivery end 22 as set in the current setting control 98. The actual pressure of the medium at the point of delivery may also be sensed by means of the pressure sensing element 27 and the output signal therefrom delivered at line 28 to the current setting control 98. The sensing element may also include means for sensing the skin temperature of the patient to whom the medium dispensed from the delivery apparatus is being administered. The signal from the line 28 further adjusts the reference pressure setting at the current setting control 98 in the same manner as described above in connection with the embodiment of FIG. 1.

In the embodiment of FIG. 2, the electric motor means 80 thus constitutes the means for generating and applying an actuating force to the push rod 62 and piston 63 of the syringe 12. The current flowing through the current sensing means 94 is directly proportional to the force output of the motor means 80 as applied to the push rod 62 and piston 63 of the delivery device apparatus 12. The magnitude of the current sensed by sensing means 94 is compared with the reference current level set at the current setting control 90 at line 99 by comparator means incorporated in the current control circuit 86, and the current control circuit 86 operates to reduce this difference to zero and thereby regulates the current flowing to the motor means 80 through the sensor 94 to the precise reference current level set at the current setting control 90.

Thus, for any selected reference current magnitude entered by an operator at the current setting control circuit 98, the current flowing to the torque motor means 80 is precisely regulated and maintained at a level corresponding to the selected reference current magnitude and, hence, the linear output force of the motor means 80 as delivered at the output rod 82 is maintained at a fixed and precisely controlled force level corresponding to the reference setting throughout the entire stroke of the push rod 62 of the syringe 12. As explained above, further adjustments in the magnitude of the reference current setting may be effected by pressure signals sensed at the delivery end 22 of the delivery device and/or at the point of administering the medium to a patient.

It is to be understood, of course, that the pressure signals at lines 25 and 28 in both of the embodiments of FIGS. 1 and 2 may be compared with the preselected reference pressure setting in any suitable manner to cause the error signal, that is the difference between the sensed pressure levels and the preselected reference pressure level, to be adjusted to zero. This may be done by readjustment of the originally set reference pressure level or by other means and all of the same are referred to herein as causing the error signal, that is the difference between the original preselected reference pressure level and the sensed pressure level, to be reduced to zero.

Thus, in both of the embodiments shown in FIGS. 1 and 2, the fluid 14 is thus delivered from the syringe 12 by the delivery apparatus of the present invention at a constant and controlled pressure throughout the entire stroke of the piston 63 within the barrel of the delivery device apparatus 12. The present invention thus provides important and significant advantages, particularly in cases where the fluid 14 is itself pressure sensitive or where treatment, diagnostic or other requirements associated with the medicinal uses of the fluid 14 are such that delivery pressure be carefully controlled. Since the apparatus of the present invention functions automatically once the desired delivery force (and corresponding delivery pressure) is set by the operator, the control of the delivery pressure does not depend upon human factors such as operator skill and/or subjective judgment, with the attendant risks of human error.

In a still further embodiment of the present invention, the sensing element, the sensing element 27 includes, in each of the embodiments of FIGS. 1 and 2, a temperature sensing means for sensing the skin temperature of the patient to whom the medium being dispensed from the delivery apparatus is being administered. In some cases, the sensitivity of the patient to the pressure of the medium being dispensed from the delivery apparatus varies and the skin temperature of the patient is an important parameter in sensing the need from that standpoint of an adjustment of the pressure of the medium or a complete shutdown of the delivery apparatus in order to avoid damage to the veins of the patient.

In this further embodiment, the skin temperature of the patient is sensed by the sensor 27 in each of the embodiments of FIGS. 1 and 2, in addition to sensing the pressure of the medium at the point of delivery, and the pressure of the medium is adjusted by the control system in response to the sensed patient skin temperature in the same manner as described above in response to the sensed pressure of the medium. In each of the embodiments of FIGS. 1 and 2, the signal at line 29 then includes or may consist exclusively of the sensed skin temperature signal from the sensing element 27.

The terms "delivery force" and "delivery pressure" are used interchangeably herein since, once a force to be applied to the push rod 62 of the syringe is set and controlled, a pressure level is generated in the fluid 14 which is a function of the force applied to the push rod 62. Thus, for any given force applied to the push rod 62, there is established a pressure in the fluid 14 which is a function of the applied force. The term "delivery force", as used herein to refer to the force applied to the delivery mechanism of the delivery device apparatus, thus has the same meaning as "delivery pressure" as applied to the medium being dispensed from the syringe, since the same are directly proportional to each other.

It is to be noted that in both of the embodiments of FIGS. 1 and 2, the means for sensing the level of the force applied to the push rod 62 and piston 63 of the delivery device apparatus 12 actually constitutes means for sensing the pressure level of the medium 14 in the delivery device apparatus 12, since the pressure level of the medium 14 is directly proportional to the level of the force applied to the push rod 62 and the piston 63. Other means for sensing the pressure level in the medium 14 may, of course, be employed but the method shown in the embodiments of FIGS. 1 and 2 allows sensing of the pressure of the medium 14 without invasion of the sterilized interior of the delivery device apparatus 12 in which the presterilized contents 14 are stored.

It is to be understood that the embodiments disclosed herein are shown and described in detail for purposes of presenting a full and complete disclosure of the present invention and that the same are not to be interpreted as limiting in any way the true scope of the present invention as defined in the appended claims.

I claim:

1. A delivery apparatus for delivering a stored medium from a variable volume delivery device in which mechanical actuating means are provided for expelling the stored medium from the delivery device through a delivery tip at one end thereof, said delivery apparatus comprising:

fixture means for receiving and positioning said delivery device;

said fixture means including force generating and application means for applying an actuating force to said mechanical actuating means of said delivery device to subject the stored medium in said variable volume chamber to a pressure for the expulsion of said medium from said chamber through said delivery tip;

said fixture means further including an opening therein for receiving said delivery tip and positioning the same for connection to a use application;

pressure sensing means for sensing and generating a signal proportional to the magnitude of the pressure in said medium resulting from the force applied by said force generating and application means;

reference pressure generating means for generating a reference pressure signal representing a preselected desired reference pressure magnitude for the pressure in said medium resulting from the actuating force applied by said applicator means;

comparator means for comparing the signal generated by said pressure sensing means with said reference pressure signal and for generating a difference signal proportional to the difference between the signal generated by said pressure sensing means and said reference pressure signal;

control means for controlling the magnitude of the force applied by said applicator means; and means connecting said difference signal to said control means for controlling the magnitude of the force applied by said applicator means in a direction to reduce the magnitude of said difference signal to zero, whereby said applied force is automatically regulated to maintain a pressure in said medium at the level represented by said reference pressure signal.

2. A delivery apparatus as set forth in claim 1 in which said pressure sensing means includes means for sensing the pressure in said medium at a point downstream of the delivery tip of said delivery device.

3. A delivery apparatus as set forth in claim 1 in which said pressure sensing means includes means for sensing the pressure in said medium at the point of delivery to a patient.

4. A delivery apparatus as set forth in claims 1, 2 or 3 in which said force generating and application means includes a compartment and a piston and means for applying an actuating pressure to said piston and said force sensing means includes means for sensing the pressure applied to said piston.

5. A delivery apparatus as set forth in claims 1, 2 or 3 in which said force generating and application means includes an electric motor and said force sensing means includes current sensing means for sensing the current flowing to said electric motor.

6. A delivery apparatus for delivering a stored medium from a variable volume delivery device in which mechanical actuating means are provided for expelling the stored medium from the delivery device through a delivery opening thereof, said delivery apparatus comprising:

a delivery device having a variable volume chamber for storing a medium to be delivered from said delivery device;

a delivery opening connected to said variable volume chamber through which said stored medium is expelled;

said delivery device including actuating means for varying the volume of said chamber to expel the stored medium from said variable volume chamber through said delivery opening;

fixture means for receiving said delivery device;

said fixture means including force generating and application means for applying an actuating force to said actuating means of said delivery device, whereby the stored medium in said variable volume chamber is subjected to a pressure for the expulsion of said medium from said chamber through said opening;

pressure sensing means for sensing and generating a signal proportional to the magnitude of the pressure in said medium resulting from the force applied by said force generating and application means;

reference pressure generating means for generating a reference pressure signal representing a preselected desired pressure magnitude in said medium resulting from the actuating force applied by said applicator means;

comparator means for comparing the signal generated by said pressure sensing means with said reference pressure signal and for generating a difference signal proportional to the difference between the signal generated by said pressure sensing means and said reference pressure signal;

control means for controlling the magnitude of the force applied by said applicator means; and means connecting said difference signal to said control means for controlling the magnitude of the force applied by said applicator means in a direction to reduce the magnitude of said difference signal to zero, whereby said applied force is automatically regulated to maintain a pressure in said medium at the level represented by said reference pressure signal.

7. A delivery apparatus as set forth in claim 4 in which said delivery device comprises a prefilled container containing a pressure sensitive medium to be dispensed from the container.

8. A delivery apparatus as set forth in claims 6 or 7 in which said pressure sensing means includes means for sensing the pressure in said medium at a point downstream of the delivery tip of said delivery device.

9. A delivery apparatus as set forth in claims 6 or 7 in which said pressure sensing means includes means for sensing the pressure in said medium at the point of delivery to a patient.

10. A delivery apparatus as set forth in claim 1 further including temperature sensing means for sensing the skin temperature of a patient to whom the medium is being administered and for adjusting the delivery pressure of said medium in response to said temperature sensing means.

* * * * *